United States Patent
Van Der Zaag et al.

(10) Patent No.: US 8,784,623 B2
(45) Date of Patent: Jul. 22, 2014

(54) NANOPORE DEVICE AND A METHOD FOR NUCLEIC ACID ANALYSIS

(75) Inventors: Pieter Jan Van Der Zaag, Eindhoven (NL); Anja Van De Stolpe, Eindhoven (NL); Elaine McCoo, Eindhoven (NL); Eva Van Van Wanrooij, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 496 days.

(21) Appl. No.: 13/003,308

(22) PCT Filed: Feb. 17, 2009

(86) PCT No.: PCT/IB2009/050635
§ 371 (c)(1),
(2), (4) Date: Jan. 10, 2011

(87) PCT Pub. No.: WO2010/007537
PCT Pub. Date: Jan. 21, 2010

(65) Prior Publication Data
US 2011/0108423 A1    May 12, 2011

(30) Foreign Application Priority Data

Jul. 17, 2008 (EP) .................................. 08160644

(51) Int. Cl.
*G01N 27/327* (2006.01)
(52) U.S. Cl.
USPC .................................... 204/403.01; 204/409

(58) Field of Classification Search
USPC ................. 204/403.01, 409–412, 603, 452
See application file for complete search history.

(56) References Cited

U.S. PATENT DOCUMENTS

| | | | |
|---|---|---|---|
| 2007/0042366 A1* | 2/2007 | Ling | 435/6 |
| 2007/0048754 A1 | 3/2007 | Freeman et al. | |
| 2007/0054276 A1 | 3/2007 | Sampson | |
| 2007/0159156 A1* | 7/2007 | Hu et al. | 324/71.1 |
| 2008/0025875 A1 | 1/2008 | Martin et al. | |
| 2008/0119366 A1 | 5/2008 | Sauer et al. | |

FOREIGN PATENT DOCUMENTS

| | | |
|---|---|---|
| DE | 102006035072 A1 | 7/2006 |
| EP | 1645628 A1 | 4/2006 |
| WO | 2007117832 A2 | 10/2007 |

OTHER PUBLICATIONS

By D. Branton et al.; "The Potential and Challenges of Nanopore Sequencing" Nature Biotechnology; vol. 26 No. 10 October 2008; http://www.nature.com/naturebiotechnology; pp. 1146-1153.

By Y. Astier et al.; "Toward Single Molecule DNA Sequencing: Directing Identification of Ribonucleoside and Deoxyribonucleoside 5'-Monophosphates by Using an Engineered Protein Nanopore Equipped With a Molecular Adapter"; Contribution from the Department of Chemistry, University of Oxford, Chemistry Research Laboratory, Mansfield Road, OX1 3TA, Oxford, UK Received Oct. 19, 2005; E-mall: hagan.bayley@chem.ox.ac.uk. pp. 1705-1710.

(Continued)

*Primary Examiner* — Alex Noguerola

(57) ABSTRACT

A nanopore device is described wherein is provided a sample input (110), an input chamber (120), and first and second sample chambers (130, 140) connected to the input chambers (120) via first and second nanopores (135, 145).

6 Claims, 4 Drawing Sheets

(56) References Cited

OTHER PUBLICATIONS

By S. Howorka et al.; Sequence-Specific Detection of Individual DNA Strands Using Engineered Naopores; Nature Publishing Group http://blotech.nature.com; Department of Medical Biochemistry and Genetics, The Texas A&M University System Health Science Center, 440 Reynolds Medical Building, College Station, TX 77843-1114. Department of Chemistry, Texas A&M University, College Station, TX 77843-3255. Corresponding Author (howorlai/medicine.tamu.edu). p. 636-639.

R, Henriquez et al. "The Resurgence of Coulter Counting for Analyzing Nanoscale Objects"; The Royal Society of Chemistry 2004; Depatrtment of Chemistry, Texas A&M University, P.O. Box 30012, College Station, TX 77842-3012, USA E-mail: crooks@tamn.edu; Tel: voice: 979-845-5629; Fax: 979-845-1399; pp. 478-482.

* cited by examiner

NANOPORE DEVICE AND A METHOD FOR NUCLEIC ACID ANALYSIS

FIELD OF THE INVENTION

The invention relates to the field of determining information from nucleic acid material, for example genetic material such as DNA. In particular, the invention relates to the field of rapid nucleic acid analysis by means of a nanopore device.

Specifically the invention relates to a nanopore device, arranged to cooperate with a sample of genetic material, the nanopore device comprising an input chamber, for containment of the sample of nucleic acid a first chamber connected to the input chamber by a first nanopore means to apply an electrical potential difference across the first nanopore, the electrical potential being arranged to draw a first fragment of the sample of genetic material through the first nanopore an electrolytic solution which is capable of flow through the first nanopore under the influence of the electrical potential difference, the flow detectable as a first ionic current, changes in the first ionic current being indicative of detection of a first target molecule by the first nanopore

BACKGROUND OF THE INVENTION

The structure and composition of nucleic acid material, including genetic material, especially gene sequencing and the identification of genetic markers associated with specific disease, is becoming more important. Within biomedical and pharmaceutical industries and associated research, more emphasis is being placed on accurate and speedy gathering of information. In particular the genetic patterns connected with disease or reactions to medications should be accessed quickly with an aim to provide genetic information for point-of-care applications. Methods and devices are being developed to facilitate this.

It has been discovered that biosensor elements can be capable of identifying individual DNA strands with single base resolution, a base being one of four possible types of molecules (A, C, G or T) used to encode information in the DNA. In particular, so-called nanopores are utilized. These are apertures in a thin layer, typically 100 nm or smaller, formed in many possible geometrical shapes. Segments of the genetic material to be sequenced are passed through or forced through the aperture. The shape of the samples or the temporary binding of the molecules of the samples with the molecules of the nanopore cause registration in the detection device characteristic of the various bases, thereby facilitating sequencing. A nanopore may be biological or synthetic in origin. Each nanopore is specific for a desired detection and can therefore be made into a detector for a specific gene sequence, such as that associated with a particular cancer mutation, or for an SNP (single nucleotide polymorphism), for example associated with a drug response in anaesthesia or chemotherapy. The use of nanopores allows rapid detection compared with current sequencing devices.

US patent application 2007/0054276 discusses polynucleotide analysis systems and methods of nanopore analysis, and how to rapidly determine the sequence of a nucleic acid molecule for identifying genetic mutations and polymorphisms. It discloses the concept of nanopore sequencing as based in the property of physically sensing the individual nucleotides or physical changes in the environment of the nucleotides (e.g. electric current) within an individual polynucleotide as it traverses through a nanopore aperture. The SNP can be identified using the nanopore analysis system to measure an electronic signature (e.g. ion current or tunneling current) of the modified target polynucleotides, the electronic signatures of modified and non-modified molecules being distinguishable. The nanopore detection system used comprises electronic equipment capable of measuring the electronic characteristics of the interaction between nanopore aperture in a structure of the nanopore detection system and the polynucleotide. A computer system controls the electronic measurement and handles the data produced. Volume, shape or charges on each monomer can affect conductance in a characteristic way. A voltage gradient is applied to the nanopore device to draw the target polynucleotide from one side of the aperture to the other.

US patent application 2007/0048745, from the same applicant, further discloses devices, systems and methods for nanopore analysis of polymers.

Papers in J. Amer. Chem. Soc. 128 (2006) 1705 and Nature Biotech 19 (2001) 636, disclose the use of biological nanopores for sequence specific detection of individual DNA strands using engineered nanopores. Binding of the DNA strand molecules to molecules in the nanopore causes changes in an ionic current flowing through the nanopore.

Present work focuses on a nanopore detection and readout for a specific gene sequence. The devices make only one specific measurement on a sample.

A problem with these current devices and methods is that acquiring information for more than one target sequence is slow, requiring repetitive measurements.

It is thus an object of the invention to provide an improved device which can provide more sequencing information, faster.

SUMMARY OF THE INVENTION

According to the invention this object is achieved by provision of a second chamber connected to the input chamber by a second nanopore the electrical potential difference being applied across the second nanopore equal to, and common with, the electrical potential difference across the first nanopore, the electrical potential across the second nanopore being arranged to draw a second fragment of the sample of nucleic acid through the second nanopore and to influence the electrolytic solution to flow through the second nanopore, the flow detectable as a second ionic current, changes in the second ionic current being indicative of detection of a second target molecule by the second nanopore.

The invention allows for incorporation of a second chamber into the nanopore device. This allows two measurements to be performed simultaneously thereby obtaining sequencing information faster.

An additional advantage of this invention is that the second nanopore receives input fragments from the same input chamber as the first nanopore, therefore the samples being processed by the first and second nanopores are from the same source and have no aging effects or other processing differences which may influence the sequencing results. Examples of possible samples input to the device are polynucleotides such as DNA, RNA or uRNA. In certain instances, such as with biopsy samples, it is very disadvantageous if the sample must be split in two halves in order to run two different sequencing detections. There is the possibility that the different components of the sample may not be properly distributed between the two halves. A single sample input for both measurements removes such inaccuracies. The nucleic acid sample is not, however, restricted to natural nucleic acids. Synthetic or artificial nucleic acids may also be used as samples.

Yet another advantage of this invention is that the electrical potential difference being applied across the first and second nanopores is the same. This consistency improves the functioning of the device and the reliability of the measurements obtained. The fragments passing through each nanopore are subject to the same forces and the electrolytic solution is drawn through the nanopores at the same rate under electrical field with similar properties.

The electrical potential difference may be applied from the same voltage supply or different voltage supplies. The voltage supply may be internal or external to the device.

The invention is described in terms of a first and a second chamber, but is not limited to two chambers as there could be a third, fourth, fifth or nth number of chambers connected to the input chamber via a third, fourth, fifth or nth number of nanopores, all made subject to the same electrical potential.

The nanopores may be biological or synthetic. Each nanopore is by definition designed to detect specific target molecules. (For example the paper by Howorka, Cheley and Bayley in Nature Biotech 19 (2001) 636 discusses how binding of single stranded DNA (ssDNA) molecules to tethered DNA stand is achieved by covalent attachment within the lumen of an alpha-hemolysin pore of an individual DNA oligonucleotide). The active detection component of the nanopore may, for example, be a natural or an artificial nucleic acid. In the invention, however, the nanopores used in the various chambers may be the same as each other, completely different from each other or a weighted distribution of specific nanopores for measurements dependent on the application for which the nanopore device is used.

Biological nanopores and synthetic nanopores operate in different ways to alter the flow of an ionic current, changes in which register the detection of the presence of target molecules in sample fragments. Biological nanopores temporarily close on detection of a target molecule due to bonding between the sample fragment and the nanopore detection molecules. The bonding stops the flow of electrolytic solution through the nanopore thereby halting the flow of charge and therefore the ionic current. Synthetic nanopores are typically formed by an etched hole in a substrate, such as silicon, which becomes blocked due to the physical presence of an attached molecule only present when a target molecule is detected. Biological pores have proved useful for a range of experiments but exhibit some disadvantages such as fixed size and limited stability. External factors, such as temperature and stress can trigger this instability. Fabrication of nanopores from solid state materials allows greater control over diameter and channel length of the nanopore, and surface properties.

The connection between the input chamber and a first chamber is described above as a single nanopore but it should be understood that a connection made by a plurality of nanopores in parallel, all with equal access to the input chamber sample fragments, should not be excluded.

The nanopore device according to the invention is arranged to cooperate with a sample of nucleic acid. However, the nanopore device is also capable of cooperating with samples of other materials including, but not limited to, proteins, peptides, sugars, glyco lipids, lipids and synthetic polymers or molecules.

A "sample" in the context of the present invention may originate from a biological source. Encompassed are biological fluids such as lymph, urine, cerebral fluid, bronco leverage fluid (BAL), blood, saliva, serum, faeces or semen. Also encompassed are tissues, such as epithelium tissue, connective tissue, bones, muscle tissue such as visceral or smooth muscle and skeletal muscle, nervous tissue, bone marrow, cartilage, skin, mucosa or hair.

A "sample" in the context of the present invention may also be a sample originating from an environmental source, such as a plant sample, a water sample, a soil sample, or may be originating from a household or industrial source or may also be a food or beverage sample.

A "sample" in the context of the present invention may also be a sample originating from a biochemical or chemical reaction or a sample originating from a pharmaceutical, chemical, or biochemical composition.

The amount of sample is preferably 1000 µl or less, more preferably 500 µl or less, even more preferably 100 µl or less, most preferably 50 µl or less.

Where appropriate, as for instance in the case of solid samples or viscous suspensions, the sample may need to be solubilized, homogenized, or extracted with a solvent prior to use in the present invention in order to obtain a liquid sample. A liquid sample hereby may be a solution or suspension.

Liquid samples may be subjected to one or more pre-treatments prior to use in the present invention. Such pre-treatments include, but are not limited to dilution, filtration, centrifugation, pre-concentration, sedimentation, dialysis, lysis, eluation, extraction and precipitation.

Pre-treatments may also include the addition of chemical or biochemical substances to the solution, such as acids, bases, buffers, salts, solvents, reactive dyes, detergents, emulsifiers, chelators, enzymes, chaotropic agents.

The nanopore detection device may be applied in many circumstances but in particular is useful for:

quantitative detection of a known sequence, so-called "PCR-less" detection (PCR being a polymerase chain reaction), where the data of interest is the amount of a certain nucleotide sequence or gene present and the nanopore is setup to detect this specific sequence.

SNP (single nucleotide polymorphism) detection, where the nanopores are arranged to detect mutations in a sequence sequencing where the end goal is to determine the base pair sequence of a nucleic acid.

In a further embodiment of the invention, the nanopore device further comprises a third chamber connected to the input chamber by a third nanopore, an electrical potential difference being applied across the third nanopore equal to, and common with, the electrical potential difference across the first nanopore, the electrical potential across the third nanopore being arranged to draw a third fragment of the sample of nucleic acid through the third nanopore and to influence the electrolytic solution to flow through the third nanopore, the flow detectable as a third ionic current by the current detector, changes in the third ionic current being indicative of detection of a control target molecule for validating device measurement.

For some types of sample fragments, certain sequences are either always present or never present. To measure such sequences, or confirm their absence, gives a positive or negative indicator to support the other measurements taking place on the sample fragments. This improves the quality of the overall measurement result.

In a further embodiment of the invention, a correlating means is arranged to correlate detections indicated by changes in at least two of the ionic currents.

Each ionic current is representative of detection of a specific target molecule. The nanopore device may be arranged to detect several different target molecules using different nanopores. However, the detection of individual molecules may be more relevant or interesting if these detections occur in relation to detections of another molecule. Thus by correlating the changes in the ionic currents, extra information may be extracted.

An example of this would be the correlation over time between changes in a first and second ionic current to determine the frequency of occurrence of mutations as compared to normal genetic sequence. This would be relevant in the field of oncology, for example.

The correlating means could also be used to compare detection of positive or negative indicators (for example the third ionic current) with sample detections (for example the first and/or second ionic currents) to confirm valid device functioning.

In a further embodiment of the invention, the first target molecule is a selected wild type gene sequence and the second target molecule is a specific mutation in the same gene sequence, for relative detection of the statistical occurrence of the mutation.

This is a particular embodiment of the device directed to the study of two types of DNA which is important for the development of new strategies in cancer therapies. The basic sample to be analysed is comprised of at least two types of DNA, wild and mutated. The mutated sample may comprise mutations such as SNP (single nucleotide polymorphisms), deletion, or insertion of nucleotides. The device of the invention can be used to perform a simple quantitative detection of the balance at which these species occur in the sample. The extent to which a specific mutated gene (e.g. a tumour suppressor gene or oncogene) occurs in the population of cancer cells can be analysed. This could be a very important diagnostic tool in determining therapeutic decisions and allow personalised treatment—for example the mutated gene could be a proven drug target, or resection margins in surgery free from cancerous cells would be determined.

Specifically, when combined with correlation of detections of first and second target molecules, wild and mutated DNA respectively, 10 binding events for wild type sample fragment could correspond to only 3 binding events for mutated sample fragment. Investigation of this information by correlating detections over a time period of for example 1 hour, would then prompt the conclusion that 3/13 or approximately 23% of the sample studied contains defective mutated material. This figure would be relevant for a clinical decision.

In a further embodiment of the invention, at least one of the nanopores is a biological nanopore.

In a further embodiment of the invention, the biological nanopore is arranged in cooperation with a lipid bilayer.

A method based on biological nanopores according to the invention, would be applicable to a small sequencing device for simple, rapid and inexpensive mutation detection, particularly at point of care.

In another aspect of the invention, there is provided a method of manufacturing a nanopore device comprising the steps of:
providing an input chamber for containing a sample of nucleic acid
providing a first chamber connected to the input chamber by a first nanopore
providing an electrolytic solution capable of flow through the first nanopore under the influence of an electric potential difference
providing a means to apply an electrical potential difference across the first nanopore
providing a second chamber connected to the input chamber by means of a second nanopore and in that
arranging the means to apply the electrical potential difference across the second nanopore equal to and common with the electrical potential across the first nanopore.

The invention allows for incorporation of a second chamber into the nanopore device. This allows two measurements to be performed simultaneously thereby obtaining sequencing information faster.

An advantage of this invention is that the electrical potential difference being applied across the first and second nanopores is the same. This consistency improves the functioning of the device and the reliability of the measurements obtained. The fragments passing through each nanopore are subject to the same forces and the electrolytic solution is drawn through the nanopores at the same rate under electrical field with similar properties.

The electrical potential difference may be applied from the same voltage supply or different voltage supplies. The voltage supply may be internal or external to the device.

The invention is described in terms of a first and a second chamber, but is not limited to two chambers as there could be a third, fourth, fifth or nth number of chambers connected to the input chamber via a third, fourth, fifth or nth number of nanopores, all made subject to the same electrical potential.

The nanopores may be biological or synthetic. Each nanopore is by definition designed to detect specific target molecules. The active detection component of the nanopore may, for example, be a natural or an artificial nucleic acid. In the invention, however, the nanopores used in the various chambers may be the same as each other, completely different from each other or a weighted distribution of specific nanopores for measurements dependent on the application for which the nanopore device is used.

Biological pores have proved useful for a range of experiments but exhibit some disadvantages such as fixed size and limited stability. External factors, such as temperature and stress can trigger this instability. Fabrication of nanopores from solid state materials allows greater control over diameter and channel length of the nanopore, and surface properties.

The connection between the input chamber and a first chamber is described above as a single nanopore but it should be understood that a connection made by a plurality of nanopores in parallel, all with equal access to the input chamber sample fragments, should not be excluded.

In another aspect of the invention, there is provided a method of using a nanopore device wherein a wild gene sequence is detected by means of the first nanopore and a specific mutation of said gene sequence is detected by means of the second nanopore This is a particular embodiment of the device directed to the study of two types of DNA which is important for the development of new strategies in cancer therapies. The basic sample to be analysed is comprised of two types of DNA, wild and mutated, and the device of the invention can be used to perform a simple quantitative detection of the balance at which these species occur in the sample. The extent to which a specific mutated gene (e.g. a tumour suppressor gene or oncogene) occurs in the population of cancer cells can be analysed. This could be a very important diagnostic tool in determining therapeutic decisions and allow personalised treatment—for example the mutated gene could be a proven drug target, or resection margins in surgery free from cancerous cells would be determined.

In another aspect of the invention there is provided a method of correlating detections indicated by changes in at least one of the first or second ionic currents and the third ionic current to generate a signal indicative of a valid device measurement.

The correlating means could also be used to compare detection of positive or negative indicators (for example the third ionic current) with sample detections (for example the first and/or second ionic currents) to confirm valid device functioning.

For some types of sample fragments, certain sequences are either always present or never present. To measure such sequences, or confirm their absence, gives a positive or negative indicator to support the other measurements taking place on the sample fragments. This improves the quality of the overall measurement result.

In another aspect of the invention, there is provided a method of correlating detection indicated by changes in at least two of the ionic currents to generate a comparative relation between ionic currents.

An example of this would be the correlation over time between changes in a first and second ionic current to determine the frequency of occurrence of mutations as compared to normal genetic sequence. This would be relevant in the field of oncology, for example.

As an example, when combined with correlation of detections of first and second target molecules, wild and mutated DNA respectively, 10 binding events for wild type sample fragment could correspond to only 3 binding events for mutated sample fragment. Investigation of this information by correlating detections over a time period of for example 1 hour, would then prompt the conclusion that 3/13 or approximately 23% of the sample studied contains defective mutated material. This figure would be relevant for a clinical decision.

BRIEF DESCRIPTION OF THE DRAWINGS

The invention will now be further elucidated with reference to the drawings.

Where features are consistent between drawings the numbering of reference signs has been kept consistent.

DETAILED DESCRIPTION OF EMBODIMENTS

Figure 1:
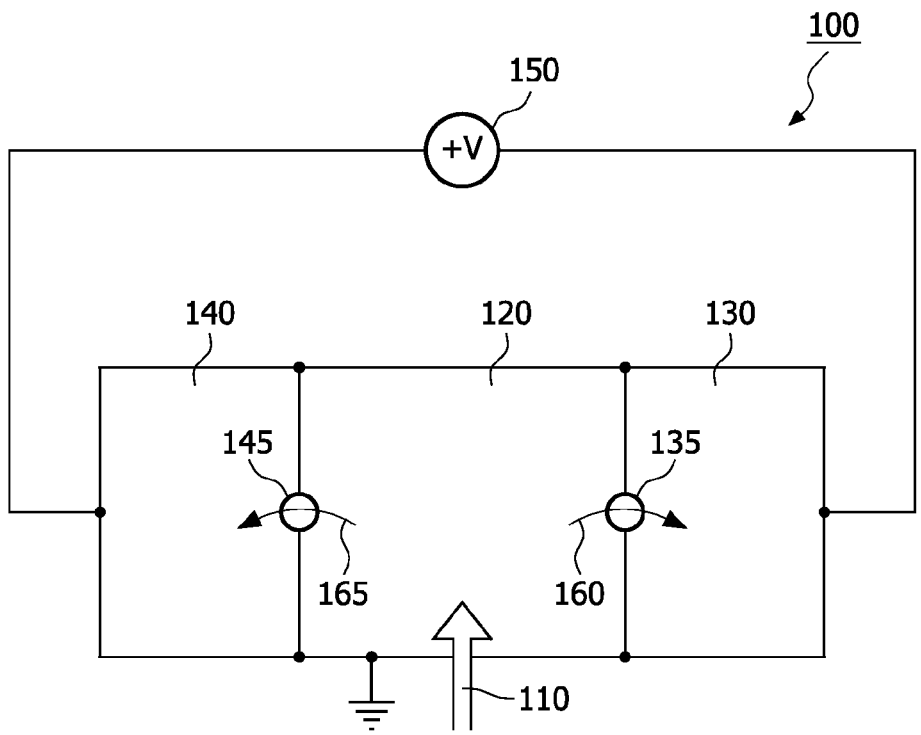
FIG. 1 illustrates a nanopore device according to the invention.

FIG. 1 depicts a nanopore device 100 according to the invention. The device comprises a sample input 110 for inputting a sample of nucleic acid material (not shown), such as DNA, RNA or uRNA, which is prepared into small fragments (not shown), into an input chamber 120. For DNA these small fragments have a negative electric charge. The input chamber 120 is arranged to be connected to a first sample chamber 130 via a first nanopore 135 and to a second sample chamber 140 via a second nanopore 145. The nanopores 135, 145 further comprise specific detection molecules (not shown) which are tailored to the required detection function of the nanopore. An electrolytic solution (not shown) is present in the chambers 120, 130, 140 and comprises charged particles. Means to apply an electrical potential difference 150 are arranged so that an electrical potential difference is present across both nanopores 135, 145. (This means to apply an electrical potential difference is shown here as internal to the nanopore device 100, but this should not be construed as limiting as an external means may also be used if desired). The electrical potential difference across the second nanopore 145 is equal to and common with the electrical potential difference across the first nanopore 135. The effect of the electrical potential difference is to draw ions of the electrolytic solution through the nanopores 135, 145 and to also draw small fragments of the sample individually through the nanopores 135, 145. Usually the sample fragments are negatively charged, as for DNA, which results in the means to apply an electrical potential being arranged so that the input chamber 120 side of the nanopores 135, 145 is at an earth potential and the first 130 and second 140 chamber sides of the nanopores are at a positive potential in order to draw the charged sample through the nanopores 135, 145 in the correct direction, here indicated by arrows 160 and 165. (However, this is only one example of the possible arrangements of the means to apply electrical potential. It will be understood that a negative to positive voltage drop may be achieved in other ways, and that depending on the sample to be analysed, a reverse electrical potential may be suitable). As the electrolytic solution is drawn through each of the nanopores 135 and 145, an ionic current is generated. Thus flow through the first nanopore 135 gives rise to a first ionic current and flow through the second nanopore 145 gives rise to a second ionic current. Detection of target molecules by the nanopores 135, 145 results in a change in this ionic current. For the present example of DNA sequencing, the biological nanopore will temporarily close on detection thereby blocking the flow of the electrolytic solution and temporarily stopping the ionic current. This ionic current and flow stoppage is detected by a means for current detection (not shown).

The commonality of the sample input chamber 120 allows different measurements and detections to be performed on the same sample in the same time period. This is beneficial for consistency of measurements results and avoids issues of splitting samples which can affect the statistical distributions of target molecules within the sample. Further the application of a common electrical potential difference ensures different measurements performed by the different nanopores are performed under the same external conditions. This aids reliability and accuracy of the data determined by the nanopore device.

Note that the input chamber 120 and first 130 and second 140 chambers are shown in FIG. 1 as being linear and two dimensional in layout and square in shape. This should not be construed as limiting as the invention allows for any shape of chambers 120 130 140 and for the chambers to be arranged also in three dimensions, depending on the requirements of the nanopore device 100.

Figure 2:
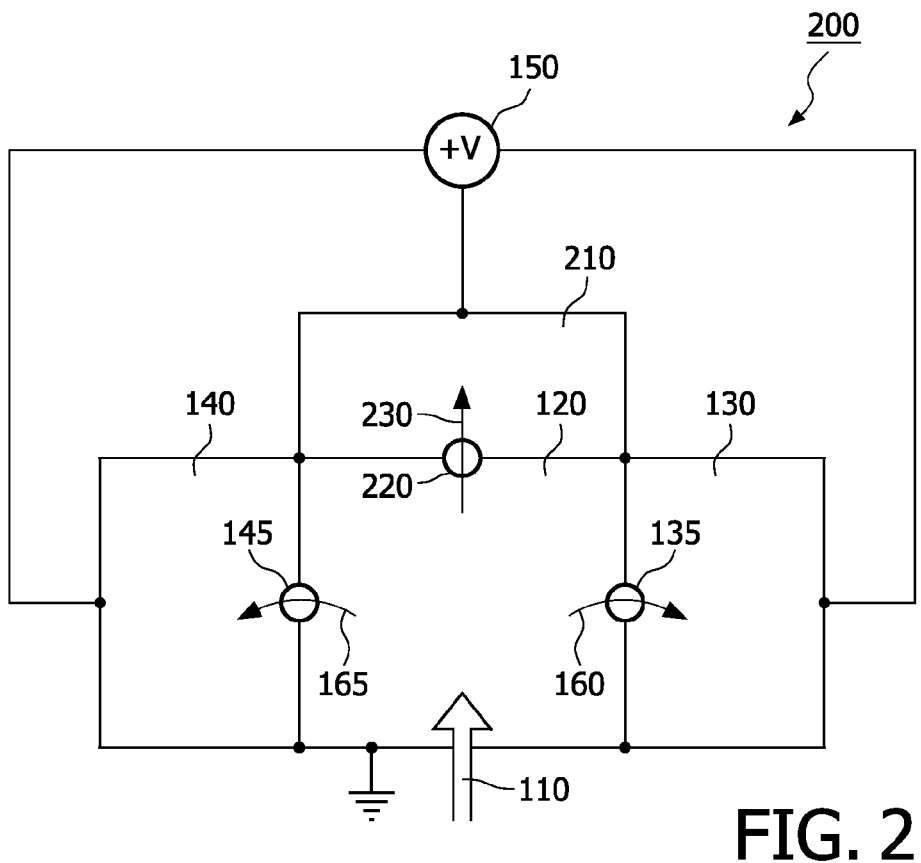
FIG. 2 illustrates a further embodiment of the invention comprising means to perform a control on the validity of device measurement

FIG. 2 shows a further embodiment of the invention comprising a nanopore device 200. This device is an extension of nanopore device 100 and comprises the same features of this device. Nanopore device 200 is, however, augmented by the addition of a third chamber 210 which is connected to the input chamber 120 by a third nanopore 220. This nanopore allows flow of the electrolytic solution (not shown) and passage of sample fragments (not shown) in the direction of the arrow 230. (Again, this is the direction for the specific example as described in FIG. 1 and should not be construed as limiting for the nanopore device 200). The nanopore 220 operates in the same manner as nanopores 135, 145, as previously described, and gives rise to a third ionic current for detection.

In this embodiment the third nanopore 220 comprises a detection molecule or mechanism to detect a specific sequence which is always present in a sample fragment regardless of genetic mutation. Thus this nanopore registers a detection for the passage of each sample fragment passing through it. This gives a positive result which can be used as a validity check for functioning of the nanopore device 200. The result can be input to a correlating means (not shown) for computed comparison with the detections from the other nanopores 135 145.

Such a validity check using the third chamber setup is not restricted to a positive measurement result. The third nanopore 220 may also be engineered to detect a sequence where a negative detection result is expected, depending on the application of the nanopore device 200.

Again, the shape of the chambers 130, 140, 210 are not limited to the shape and design as illustrated, and the layout may be arranged in two or three dimensions.

Figure 3:
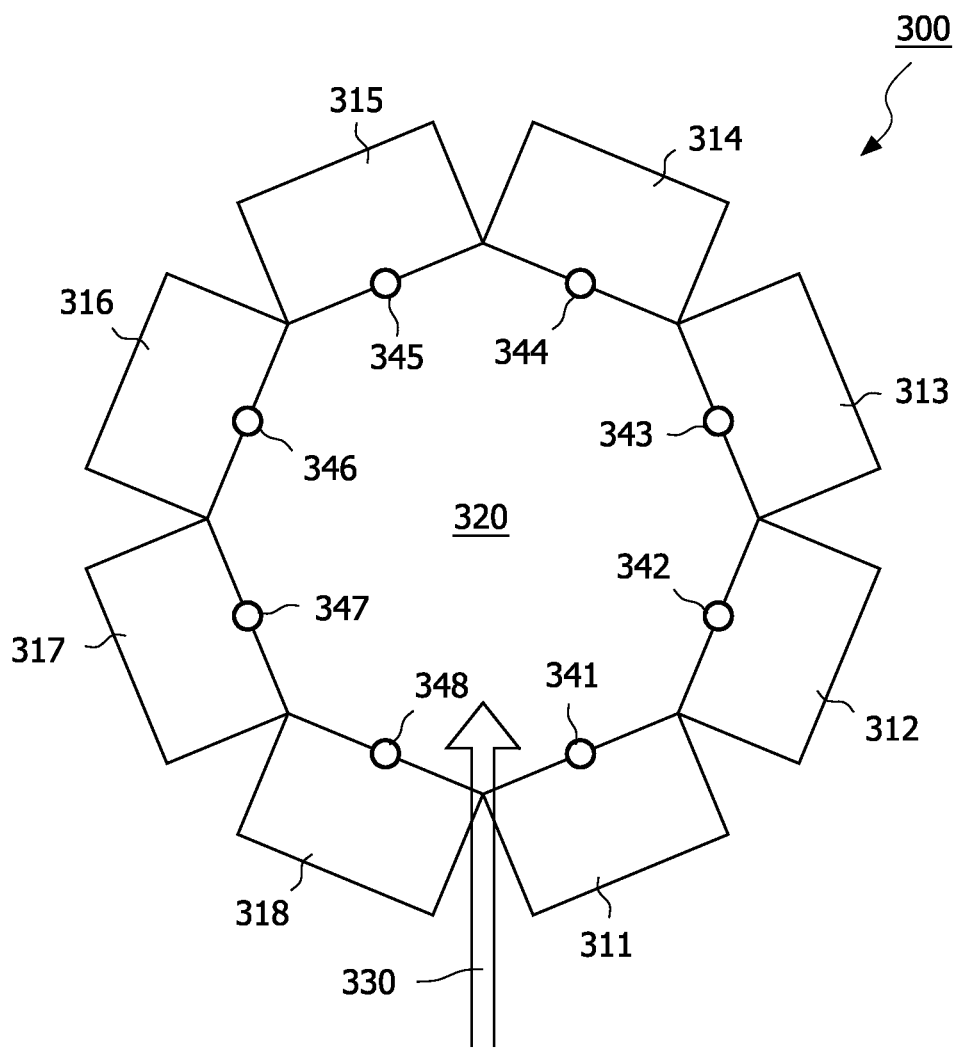
FIG. 3 illustrates a further embodiment of the invention comprising a plurality of chambers

FIG. 3 illustrates another possible embodiment of the invention wherein the nanopore device 300 comprises multiple chambers 311, 312, 313, 314, 315, 316, 317, 318 around a central input chamber 320. Each of the chambers 311, 312, 313, 314, 315, 316, 317, 318 is independent of the other chambers but each chamber is connected to the input chamber 320 by a nanopore, there being provided for each chamber a single nanopore 341, 342, 343, 344, 345, 346, 347, 348, respectively. (The invention should not be construed as being limited to a single nanopore as shown here, or in any other embodiment, but may be arranged to have multiple nanopore openings in parallel to connect each chamber to the input chamber). The nanopores 341, 342, 343, 344, 345, 346, 347, 348 are subject to the same electrical potential difference and are arranged to operate in the same manner as explained previously. (Means to apply an electrical potential difference are not shown). Ionic currents are generated for each nanopore, via electrolytic solution flow through the nanopores (not shown), which are detected and changes in these currents indicate detection of target molecules in the sample (not shown).

Figure 4:
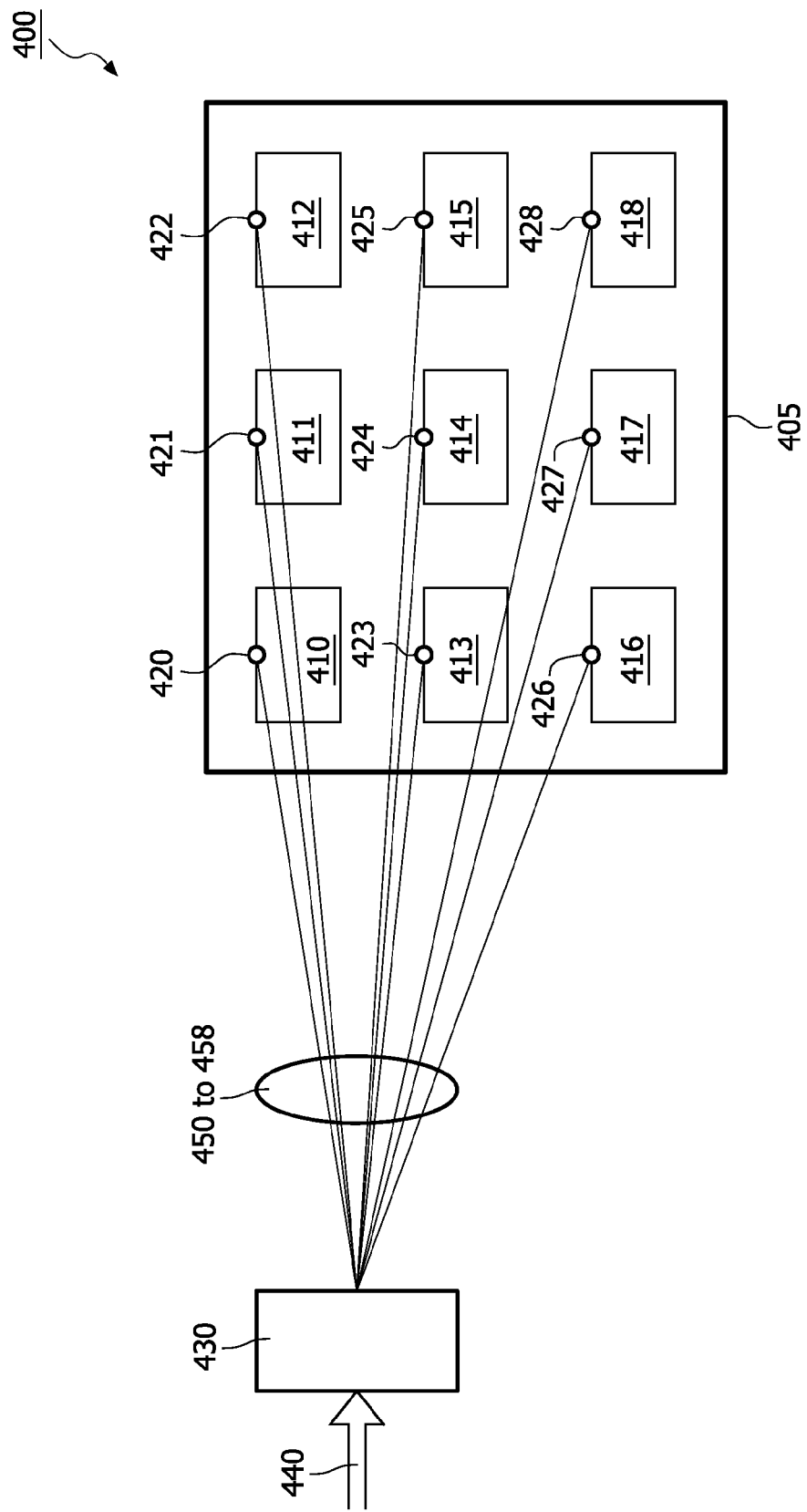
FIG. 4 illustrates a further embodiment of the invention where the chambers are arranged in the form of an array

FIG. 4 depicts a further embodiment of the invention where the nanopore device 400 comprises an array 405 comprising individual chambers 410, 411, 412, 413, 414, 415, 416, 417, 418 each remotely connected to an input chamber 430 with sample input 440 via nanopores 420, 421, 422, 423, 424, 425, 426, 427, 428, respectively. The same electrical potential difference is arranged to be applied across the nanopores 420, 421, 422, 423, 424, 425, 426, 427, 428 from a common means to apply an electrical potential (not shown). Nanopore device 400 further comprises connection means, here shown as individual conduits 450, 451, 452, 453, 454, 455, 456, 457, 458, 459 but not limited to this specific embodiment, to guide samples from the input chamber to the individual chambers 410, 411, 412, 413, 414, 415, 416, 417, 418, respectively. The operation of the nanopores and means associated with this operation (e.g. ionic current detection) are as described previously. The array 405 may be supported on a substrate (not shown) which may also comprises means (not shown) to direct the flow of sample between input 430 and chambers 410, 411, 412, 413, 414, 415, 416, 417, 418.

Figure 5:
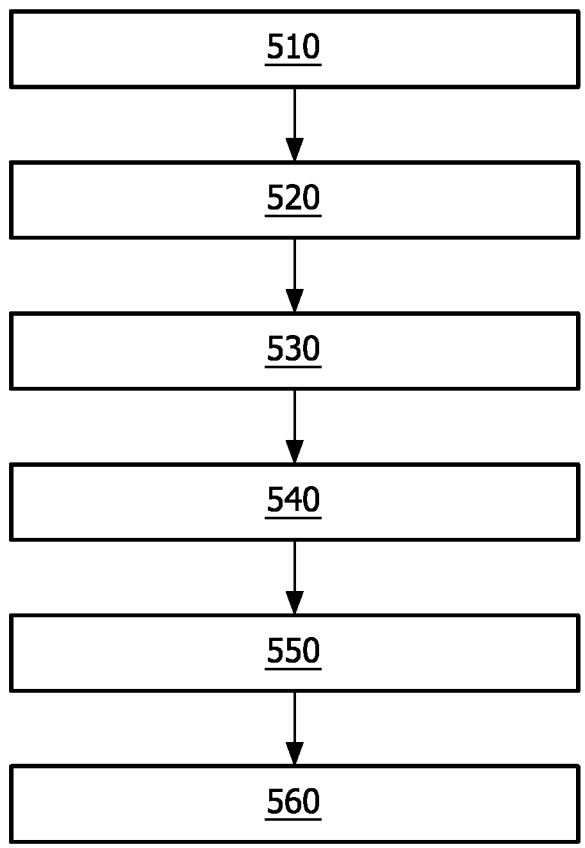
FIG. 5 illustrates a method of manufacturing a nanopore device according to the invention

FIG. 5 illustrates a method of manufacturing a nanopore device according to the invention. The method involves providing an input chamber for containing a sample of nucleic acid 510, providing a first chamber connected to the input chamber by a first nanopore 520, providing an electrolytic solution capable of flow through the first nanopore under the influence of an electric potential difference 530, providing a means to apply an electrical potential difference across the first nanopore 540, providing a second chamber connected to the input chamber by means of a second nanopore 550 and arranging the means to apply the electrical potential difference across the second nanopore equal to and common with the electrical potential across the first nanopore 560.

Figure 6:
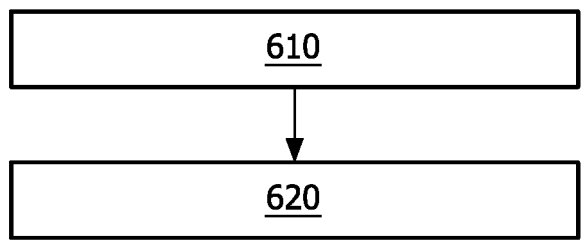
FIG. 6 illustrates a method of using a nanopore device according to the invention.

FIG. 6 illustrates a method of using a nanopore device according to the invention. This method involves detecting a wild gene sequence by means of the first nanopore 610 and detecting a specific mutation of said gene sequence by means of the second nanopore 620.

This method is especially important for determining the ration of mutated genes in a sample which can be indicative for progress of a particular cancer disease or indicative of a best treatment for personalized care.

List of Reference Numerals
100 nanopore device
110 sample input
120 input chamber
130 first chamber
135 first nanopore
140 second chamber
145 second nanopore
150 means to apply an electrical potential difference
160 arrow indicating direction of movement of a first sample fragment through the first nanopore under the influence of the electrical potential difference
165 arrow indicating direction of movement of a second sample fragment through the second nanopore under the influence of the electrical potential difference
200 nanopore device
210 third chamber
220 third nanopore
230 arrow indicating direction of movement of a third sample fragment through the third nanopore under the influence of the electrical potential difference
300 nanopore device
311 . . . 318 first to eighth chambers
320 input chamber
330 sample input
341 . . . 348 first to eight nanopores
400 nanopore device
405 array
410 . . . 418 first to ninth chambers
420 to 428 first to ninth nanopores
430 input chamber
440 sample input
450 first to ninth conduits
510 method step
520 method step
530 method step
540 method step
550 method step
560 method step
610 method step
620 method step

The invention claimed is:
1. A nanopore device, arranged to cooperate with a sample of nucleic acid, the nanopore device comprising:

an input chamber, for containment of the sample of nucleic acid;

a first chamber connected to the input chamber by a first nanopore for detecting a first target molecule;

means to apply an electrical potential difference across the first nanopore, the electrical potential being arranged to draw a first fragment of the sample of nucleic acid through the first nanopore; and an electrolytic solution which is capable of flow through the first nanopore under the influence of the electrical potential difference, the flow detectable as a first ionic current, changes in the first ionic current being indicative of detection of the first target molecule wherein, the nanopore device further comprises:

a second chamber connected to the input chamber by a second nanopore for detecting a second target molecule, the second target molecule being different from the first target molecule;

the means to apply an electrical potential difference being arranged to apply an electrical potential difference across the second nanopore which is equal to, and common with, the electrical potential difference across the first nanopore;

the electrical potential across the second nanopore being arranged to draw a second fragment of the sample of nucleic acid through the second nanopore and to influence the electrolytic solution to flow through the second nanopore; and the flow being detectable as a second ionic current, changes in the second ionic current being indicative of detection of a second target molecule by the second nanopore.

2. A nanopore device as claimed in claim 1 further comprising a third chamber connected to the input chamber by a third nanopore, an electrical potential difference being applied across the third nanopore equal to, and common with, the electrical potential difference across the first nanopore, the electrical potential across the third nanopore being arranged to draw a third fragment of the sample of nucleic acid through the third nanopore and to influence the electrolytic solution to flow through the third nanopore, the flow detectable as a third ionic current by the current detector, changes in the third ionic current being indicative of detection of a control target molecule for validating device measurement.

3. A nanopore device as claimed in claim 1 further comprising a correlating means arranged to correlate detections indicated by changes in at least two of the ionic currents.

4. A nanopore device as claimed in claim 1 wherein the first target molecule is a selected wild gene sequence and the second target molecule is a specific mutation in the same gene sequence, for relative detection of the statistical occurrence of the mutation.

5. A nanopore device as claimed in claim 1 wherein at least one of the nanopores is a biological nanopore.

6. A nanopore device as claimed in claim 5 wherein the biological nanopore is arranged in cooperation with a lipid bilayer.

* * * * *